United States Patent [19]

Yamasaki et al.

[11] Patent Number: 4,959,487
[45] Date of Patent: Sep. 25, 1990

[54] PROCESS FOR PRODUCING AROMATIC NITRILE

[75] Inventors: Hirotaka Yamasaki; Yoshio Hironaka, both of Sodegaura, Japan

[73] Assignee: Idemitsu Kosan Co., Ltd., Tokyo, Japan

[21] Appl. No.: 318,170

[22] Filed: Mar. 2, 1989

[30] Foreign Application Priority Data

Mar. 19, 1988 [JP] Japan .................................. 63-66907

[51] Int. Cl.$^5$ ........................................... C07C 253/14
[52] U.S. Cl. .................................................. 558/343
[58] Field of Search ......................................... 558/343

[56] References Cited

FOREIGN PATENT DOCUMENTS 0779330 2/1968 Canada ............................... 558/343
0110559 6/1984 European Pat. Off. ............ 558/343

Primary Examiner—Joseph P. Brust
Assistant Examiner—Mary Sue Howard
Attorney, Agent, or Firm—Frishauf, Holtz, Goodman & Woodward

[57] ABSTRACT

A process for producing aromatic nitrile, comprising reacting aromatic halide substituted by a nitro group in the ortho position relative to the halogen atom with 0.1 to 0.99 mol of cuprous cyanide and 0.1 to 2.0 mol of alkali cyanide, both being per mol of said aromatic halide, in a polar solvent, the amount of said aprotic solvent being 0.1 to 30 parts by weight per 100 parts by weight of said aromatic halide.

25 Claims, No Drawings

PROCESS FOR PRODUCING AROMATIC NITRILE

BACKGROUND OF THE INVENTION

1. Field of the Invention

The present invention relates to a process for producing aromatic nitrile and more particularly to a process for efficiently producing aromatic nitriles by reacting aromatic halides substituted by a nitro group in the ortho position relative to the halogen atom with cuprous cyanide and alkali cyanides in a polar solvent.

2. Description of the Related Art

A method of preparation of aromatic nitriles by reacting aromatic halide and cuprous cyanide is well known as the Rosenmunt von Braun reaction As one example, Chemical Abstracts, 59: 6319b describes a method of synthesizing 2-chloro-6-nitro-benzonitrile by reacting 2,3-dichloronitrobenzene and cuprous cyanide at a high temperature in a polar solvent, e.g., pyridine or dimethylformamide.

This method, however, needs more than an equimolar amount of cuprous cyanide relative to aromatic halide and further has disadvantages in that the resultant nitrile product forms an insoluble complex with the copper compound. thereby making difficult separation and the purification thereof. Moreover, it has a disadvantage in that an operation for removal of copper salts in the product by washing with ammonia water or water is complicated.

For this reason, a method in which the copper compound is oxidized by adding a divalent copper salt, or a method in which the nitrile-copper complex is decomposed by adding an excess amount of cyano compound has been employed.

SUMMARY OF THE INVENTION

An object of the present invention is to provide a process for producing aromatic nitrile.

Another object of the present invention is to provide a process for efficiently producing an aromatic nitrile using a reduced amount of cuprous cyanide.

Another object of the present invention is to provide a process for producing an aromatic nitrile, in which treatment after the cyanogenation can be easily carried out.

Still another object of the present invention is to provide a process for producing an aromatic nitrile, in which separation and purification of the product are made easier.

It has now been found that the objects can be attained by using an alkali metal cyanide along with cuprous cyanide in the reaction and performing the reaction in the presence of a limited amount of a polar solvent, and further that the product can be more easily separated and purified by extracting it with a specified solvent while it is hot.

The present invention relates to a process for producing aromatic nitrile which comprises reacting an aromatic halide substituted by a nitro group in the ortho position relative to the halogen atom with 0.1 to 0.99 mol of cuprous cyanide per mol of the aromatic halide and 0.1 to 2.0 mol of alkali cyanide per mol of the aromatic halide in the presence of 0.1 to 30 parts by weight of a polar solvent per 100 parts by weight of the aromatic halide.

DESCRIPTION OF PREFERRED EMBODIMENTS

Various aromatic halides substituted by a nitro group in the ortho position relative to the halogen atom can be used in the present invention. Usually, compounds represented by the general formula (I) as shown below are used.

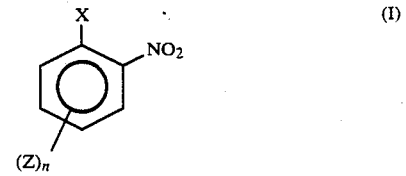

wherein X is a halogen atom, Z is a hydrogen atom, a halogen atom, an alkyl group having 1 to 4 carbon atoms, a cyano group, a hydroxyl group or a nitro group, and n is an integer of 1 to 4.

Specific examples of the halogen atom represented by X or Z are chlorine, bromine, iodine and fluorine.

Specific examples of the alkyl group having 1 to 4 carbon atoms as represented by Z are a methyl group, an ethyl group, a propyl group, an isobutyl group, a n-butyl group and a tert-butyl group.

Specific examples of the compound represented bY the general formula (I) are 2-chloronitrobenzene, 2-bormonitrobenzene, 2,3-dichloronitrobenzene, 2,4-dichloronitrobenzene, 2,5-dichloronitrobenzene, and 2,6-dichloronitrobenzene.

The amount of cuprous cyanide used in the reaction with the above aromatic halide is 0.1 to 0.99 mol, preferably 0.2 to 0.5 mol and most preferably 0.3 to 0.4 mol per mol of the aromatic halide. If the amount of cuprous cyanide in the reaction system is less than 0.1 mol, the reaction is retarded. On the other hand, if it is too large, separation of the product becomes difficult.

In the present invention, it is required that along with the above cuprous cyanide, the amount of alkali metal cyanide used be 0.1 to 2.0 mol, preferably 0.5 to 1.2 mol and most preferably 0.8 to 0.9 mol per mol of the aromatic halide.

Alkali cyanides which can be used in the present invention include sodium cyanide, potassium cyanide, potassium nickel cyanide, sodium cobalt cyanide, cesium cyanide, potassium dicyanocuprate K[Cu(CN)$_2$] and sodium dicyanocupate Na[Cu(CN)$_2$].

In the present invention, both cuprous cyanide and alkali metal cyanide are reacted with the aromatic halide in the amount ranges specified above. In general, it is preferred that the total amount of cyano group of cyanides is 1.0 to 1.4 mol per mol of the aromatic halide.

In the present invention, the reaction is carried out in the presence of a polar solvent, the amount of which is 0.1 to 30 parts by weight per 100 parts by weight of the aromatic halide as a starting material.

The reaction can be carried out in the presence of an excess amount of the a polar solvent, for example, in an amount of about 300 parts by weight per 100 parts by weight of the aromatic halide. In this case, however, unless the amount of the polar solvent is reduced to 30 parts by weight or less by a technique such as distillation during the reaction or after the completion of the reaction, separation of the product from copper compounds becomes unsuitably difficult for practical use.

If the amount of the polar solvent is too small, the reaction is retarded; that is, the rate of reaction is decreased and the reaction does not proceed efficiently. On the other hand, if it is too large, as described above, the separation of the product from copper complexes becomes difficult.

There are no special limitations as to the polar solvent to be used in the present invention, and various polar solvents can be used. For example, N,N-dimethylformamide, N,N-dimethylacetamide, N-methyl-2-pyrrolidone, N,N'-dimethylimidazolidone, dimethylsulfoxide and sulfolane can be used.

In the present invention, reaction conditions are not critical and can be chosen appropriately depending on the circumstances. The reaction is usually carried out at a temperature of 100° to 250° C. for a period of 2 to 36 hours.

Upon reaction of cuprous cyanide and alkali cyanide with the aromatic halide having a nitro group in the ortho position, the halogen atom is substituted by a cyano group. leading to the formation of the desired aromatic nitrile. That is, when the aromatic halide is a compound represented by the general formula (I), the reaction proceeds according to the following sequence:

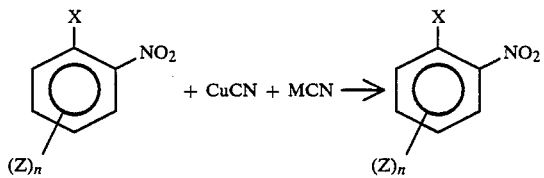

(wherein X, Z and n are the same as defined above, and M is an alkali metal).

The product is obtained by the above reaction, i.e., aromatic nitrile is extracted at a temperature of at least 70° C., if necessary, with an organic solvent having a boiling point of at least 70° C. Solvents which can be used for the extraction include aromatic compounds, e.g., benzene, toluene, xylene, chlorobenzene, dichlorobenzene and ethylbenzene; aliphatic compounds, e.g., 1,1,2-trichloroethane, or alicyclic hydrocarbons, e.g., cyclohexane. This extraction is carried out under reflux at a temperature of at least 70° C., preferably in the vicinity of the boiling point of the extraction solvent used. At a low temperature less than 70° C., the extraction efficiency is poor, and by carrying out the extraction at a temperature as near as possible to the reaction temperature, the desired product can be effectively separated from the nitrile-copper complex.

After extraction, precipitates containing copper compounds are removed by filtration. If the filtrate obtained by the filtration is subjected to post-treatment, such as washing with an alkaline aqueous solution and water, drying and removal of the solvent by the usual method, the desired aromatic nitrile is isolated.

The precipitate obtained by filtration contains cuprous cyanide, alkali cyanide, copper chloride, alkali metal chloride and their complex salts, a small amount of nitrile-copper complex, and so on. Thus, in the present invention, the precipitate is recycled to the reaction system to make good use of the unused cyanide contained in the precipitate, thereby decreasing the amount of cuprous cyanide used in each reaction. In this case, it is preferred that the precipitate be washed occasionally with water and dried well although it is not always required. If it is not washed with water, salts by-produced during the reaction (e.g., sodium chloride and potassium chloride) accumulate in the precipitate, thereby decreasing the efficiency of operation. Although a small amount of water may be present in the reaction system, it be preferred that the precipitate is recycled after drying to prevent side reactions.

In accordance with the process of the present invention, even if the amounts of cuprous cyanide and solvent used are reduced, cyanogenation of aromatic halide substituted by a nitro group in the ortho position relative to a halogen atom can be carried out with high efficiency, treatment after the reaction can be made markedly easy, and the yield of the desired nitrile can be increased.

Accordingly the process of the present invention is effective for preparation of aromatic nitrile which is useful as an intermediate for producing various medicines and industrial organic products and thus can be expected to be used in fields of e.g., organic chemical industry, agricultural chemical industry and medicine producing industry.

The present invention is described in greater detail with reference to the following examples.

EXAMPLES 1 to 8

38.4 g (0.2 mol) of 2,3-dichloronitrobenzene (DCNB), 5.37 g (0.06 mol) of copper cyanide (0.04 mole in case of EXAMPLE 4), 7.84 g (0.16 mol) of sodium cyanide and a given amount of a dry solvent were placed in a 300-milliliter three-necked flask equipped with a stirring blade and a reflux condenser, and stirred and heated up to a given temperature and reaction was maintained for a given period.

Then, 200 ml of toluene heated to 110° C. was added slowly in small portions to the reaction mixture under vigorous agitation for 1 hour at a reflux temperature of the reaction solution.

Then, the inorganic precipitate in the mixture was filtered off and washed with 50 ml of hot toluene. The filtrate thus obtained was washed with 100 ml of hot aqueous sodium hydroxide solution and filtered, and washed three times with 100 ml of distilled hot water. The toluene layer was separated and dried over 3 g of anhydrous sodium sulfate. Then, 3 g of kaolin was added and filtration was carried out by the use of a filter in which a 5 mm thick kaolin layer was placed. During all these procedure the filtrate had to be kept over 70° C. From the mother liquor thus obtained, the toluene was distilled away under reduced pressure to obtain 2-chloro-6-nitrobenzonitrile (CNBN).

The results are shown in Table 1.

TABLE 1

| No. | DCNB (mol) | CuCN (mol) | NaCN (mol) | Solvent | (g) | Temperature (°C.) | Reaction Time (hrs) | Yield*6 of CNBN (%) |
|---|---|---|---|---|---|---|---|---|
| Example 1 | 0.2 | 0.06 | 0.16 | DMF*1 | 5.7 | 180 | 8 | 91 |
| Example 2 | 0.2 | 0.06 | 0.16 | DMF | 2.9 | 180 | 24 | 82 |
| Example 3 | 0.2 | 0.06 | 0.16 | DMF | 11.3 | 180 | 8 | 89 |
| Example 4 | 0.2 | 0.04 | 0.16 | DMF | 5.7 | 170 | 36 | 78 |

TABLE 1-continued

| No. | DCNB (mol) | CuCN (mol) | NaCN (mol) | Solvent (g) | Temperature (°C.) | Reaction Time (hrs) | Yield[6] of CNBN (%) |
|---|---|---|---|---|---|---|---|
| Example 5 | 0.2 | 0.06 | 0.16 | NMP[2] 5.0 | 180 | 8 | 90 |
| Example 6 | 0.2 | 0.06 | 0.16 | DMSO[3] 6.0 | 180 | 8 | 86 |
| Example 7 | 0.2 | 0.06 | 0.16 | DMI[4] 8.0 | 180 | 8 | 84 |
| Example 8 | 0.2 | 0.06 | 0.16 | DMAc[5] 5.8 | 180 | 8 | 88 |

[1] N,N-Dimethylformamide
[2] N-methyl-2-pyrrolidone
[3] Dimethyl sulfoxide
[4] N,N'-dimethylimidazolidone
[5] N,N-Dimethylacetamide
[6] Yield (mole %)

COMPARATIVE EXAMPLE 1

The reaction was carried out under the same conditions as in Example 1 except that the amount of DMF added was changed to 100 g.

The reaction solution was stirred while adding 200 ml of toluene maintained at 120° C. in small portions, and extraction was continued at the reflux temperature of the reaction solution.

Then, the precipitate was filtered and washed with 50 ml of hot toluene. Upon addition of 100 ml of a 0.25N aqueous sodium hydroxide solution to the above obtained toluene mother liquor, solids were formed, and then the solids were filtered again.

Then, the toluene layer was separated, and 100 ml of hot water was added. Separation of the organic layer from the water layer was poor, and the water layer was colored brown and solids were formed therein.

Separation and washing with water of the toluene layer was repeated five times until the color of the water layer disappeared and precipitation of solids was not observed.

The organic layer was separated and was subjected to dehydration by adding anhydrous sodium sulfate. Then, 3 g of kaolin was added, and filtration was applied by the use of a filter in which a 5 mm thick kaolin layer was placed. The toluene was distilled away under reduced pressure from the mother liquor thus obtained to obtain 17.5 g (0.092 mol) of CNBN (purity: 96%). The yield based on DCNB was 46.0%.

COMPARATIVE EXAMPLE 2

The reaction was carried out under the same conditions as in Example 1 except that the amount of copper cyanide was changed to 0.19 g (0.022 mol) and the amount of sodium cyanide was changed to 9.8 g (0.2 mol).

The cyanation reaction almost did not proceed, and the yield based on DCNB was 3%.

EXAMPLE 9

5.66 g of DMF was added to 38.4 g (0.2 mol) of DCNB, about 14 g of the brown powder obtained in Example 1, 0.57 g (0.006 mol) of copper cyanide, and 9.84 g (0.2 mol) of sodium cyanide, and the same reaction and treatment as in Example 1 were carried out to obtain 31.0 g (0.165 mol) of CNBN (purity: 97%).

The yield based on DCNB was 82.4%.

EXAMPLE 10

4.72 g of DMF was added to 5.1 g of a precipitate obtained by washing with water about 20 g of the brown powder obtained by filtration in the above example, 38.4 g (0.2 mol) of DCNB, 0.9 g (0.01 mol) of copper cyanide, and 9.84 g (0.2 mol) of sodium cyanide, and the reaction and treatment were carried out in the same manner as in Example 1 to obtain 31.5 g (0.169 mol) of CNBN (purity: 98%).

The yield based on DCNB was 84.6%.

EXAMPLE 11

23.1 g (0.156 mol) of 2-nitrobenzonitrile was obtained by carrying out the same reaction and treatment as in Example 1 except that 31.5 g (0.2 mol) of 2-chloronitrobenzene was used in place of DCNB and benzene was used as an extraction solvent. The yield based on 2-chloronitrobenzene was 78.0%.

EXAMPLE 12

29.5 g (0.16 mol) of 5-chloro-2-nitrobenzonitrile was obtained by carrying out the same reaction and treatment as in Example 1 except that 38.4 g (0.2 mol) of 2,4-dichloronitrobenzene was used in place of DCNB. The yield based on 2,4-dichloronitrobenzene was 80%.

What is claimed is:

1. A process for producing an aromatic nitrile having a CN group and an $NO_2$ group on adjacent ring carbons atoms, said process comprising:
   (a) reacting at a temperature of 100° to 250° C. an aromatic halide of the formula

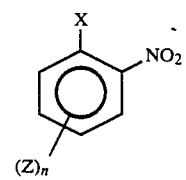

wherein X is an halogen atom, Z is a halogen atom, an alkyl group having from 1 to 4 carbon atoms, a cyano group or a nitro group, and n is an integer of 1 to 4, with 0.2 to 0.5 mol of cuprous cyanide per mol of said aromatic halide and 0.1 to 2.0 mol of a cyanide of an alkali metal per mol of said aromatic halide in 0.1 to 30 parts by weight of at least one polar solvent selected from the group consisting of N,N-dimethyl formamide, N,N-dimethylacetamide, N-methyl-2-pyrrolidone, N,N'-dimethylimidazolidone, dimethylsulfoxide and sulfolane per 100 parts by weight of said aromatic halide to form a reaction product;
   (b) extracting said reaction product from the resultant mixture at a temperature of at least 70° C. with an organic solvent having a boiling point of not less than 70° C.;
   (c) washing the extracted solution with an alkaline aqueous solution and water, and (d) removing solvent and aqueous wash solution to obtain said aromatic nitrile.

2. The process as claimed in claim 1 wherein the aromatic halide is at least one compound selected from the group consisting of 2-chloronitrobenzene, 2-romonitrobenzene, 2,3-dichloronitrobenzene, 2,4-dichloronitrobenzene, 2,5-dichloronitrobenzene and 2,6-dichloronitrobenzene.

3. The process as claimed in claim 1 wherein the alkali cyanide is at least one compound selected from the group consisting of sodium cyanide, potassium cyanide, potassium nickel cyanide, sodium cobalt cyanide, cesium cyanide, potassium dicyanocuprate and sodium dicyanocuprate.

4. The process as claimed in claim 1 wherein the solid precipitate remaining after hot extraction is recycled into the reaction system.

5. The process as claimed in claim 4 wherein said solid precipitate is recycled into the reaction system after washing with water and drying.

6. The process as claimed in claim 1, wherein said said alkali metal cyanide is in an amount of 0.5 to 1.2 mol per mol of said aromatic halide.

7. The process as claimed in claim 6 wherein the aromatic halide is at least one compound selected from the group consisting of 2-chloronitrobenzene, 2-romonitrobenzene, 2,3-dichloronitrobenzene, 2,4-dichloronitrobenzene, 2,5-dichloronitrobenzene and 2,6-dichloronitrobenzene; and said alkali cyanide is at least one compound selected from the group consisting of sodium cyanide, potassium cyanide, potassium nickel cyanide, sodium cobalt cyanide, cesium cyanide, potassium dicyanocuprate and sodium dicyanocuprate.

8. The process as claimed in claim 7 wherein said cuprous cyanide is in an amount of 0.3 to 0.4 mol per mol of said aromatic halide, said alkali metal cyanide is in an amount of 0.8 to 0.9 mol per mol of said aromatic halide and wherein the total amount of the cyano group of said cuprous cyanide and said alkali metal cyanide is 1.0 to 1.4 mol per mol of said aromatic halide.

9. The process as claimed in claim 8 wherein said aromatic halide is 2,3-dichloronitrobenzene and wherein said aromatic nitrile is 2-chloro-6-nitrobenzonitrile.

10. The process as claimed in claim 8 wherein said aromatic halide is 2-chloronitrobenzene and wherein said aromatic nitrile is 2-nitrobenzonitrile.

11. The process as claimed in claim 8 wherein said aromatic halide is 2,4-dichloronitrobenzene and wherein said aromatic nitrile is 5-chloro-2-nitrobenzonitrile.

12. The process as claimed in claim 8 wherein said alkali metal cyanide is sodium cyanide.

13. The process as claimed in claim 5 wherein said cuprous cyanide is in an amount of 0.2 to 0.5 mol per mol of said aromatic halide and said alkali metal cyanide is in an amount of 0.5 to 1.2 mol per mol of said aromatic halide.

14. The process as claimed in claim 13 wherein the aromatic halide is at least one compound selected from the group consisting of 2-chloronitrobenzene, 2-bormonitrobenzene, 2,3dichloronitrobenzene, 2,4-dichloronitrobenzene, 2,5-dichloronitrobenzene and 2,6-dichloronitrobenzene; and said alkali metal cyanide is at least one compound selected from the group consisting of sodium cyanide, potassium cyanide, potassium nickel cyanide, sodium cobalt cyanide, cesium cyanide, potassium dicyanocuprate and sodium dicyanocuprate.

15. The process as claimed in claim 14 wherein said cuprous cyanide is in an amount of 0.3 to 0.4 mol per mol of said aromatic halide, said alkali metal cyanide is in an amount of 0.8 to 0.9 mol per mol of said aromatic halide and wherein the total amount of the cyano group of said cuprous cyanide and said alkali metal cyanide is 1.0 to 1.4 mol per mol of said aromatic halide.

16. The process as claimed in claim 15 wherein said aromatic halide is 2,3-dichloronitrobenzene and wherein said aromatic nitrile is 2-chloro-6-nitrobenzonitrile.

17. The process as claimed in claim 15 wherein said aromatic halide is 2-chloronitrobenzene and wherein said aromatic nitrile is 2-nitrobenzonitrile.

18. The process as claimed in claim 15 wherein said aromatic halide is 2,4-dichloronitrobenzene and wherein said aromatic nitrile is 5-chloro-2-nitrobenzonitrile.

19. The process as claimed in claim 16 wherein said alkali metal cyanide is sodium cyanide.

20. The process as claimed in claim 1 wherein said organic extracting solvent is selected from the group consisting of benzene, toulene, xylene, chlorobenzene, dichlorobenzene and 1,1,2 trichloroethane.

21. The process as claimed in claim 8 wherein said organic extracting solvent is selected from the group consisting of benzene, toulene, xylene, chlorobenzene, dichlorobenzene and 1,1,2 trichloroethane.

22. The process as claimed in claim 21 wherein said aromatic halide is 2,3-dichloronitrobenzene and wherein said aromatic nitrile is 2-chloro-6-nitrobenzonitrile.

23. The process of claim 1 wherein the reaction of step (a) is performed over a period of between 2 and 36 hours.

24. The process of claim 6 wherein the total amount of the cyano group derived from said cuprous cyanide and said alkali metal cyanide is 1.0 1.4 mol per mol of said aromatic 25. A process for producing an aromatic nitrile comprising
(a) reacting at a temperature of 100° to 250° C. and aromatic halide of the formula

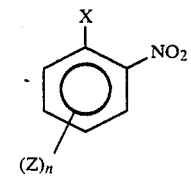

for a period of between 2 and 36 hours with 0.3 to 0.4 mol of cuprous cyanide and 0.8 to 0.9 mol of a cyanide of an alkali metal, per mol of said aromatic halide, the total amount of the cyano group derived from the cuprous cyanide and the alkali metal cyanide being 1.0 to 1.4 mol per mol of said aromatic halide, and 0.1 to 30 parts by weight of at least one polar solvent selected from the group consisting of N,N-dimethyl formamide, N,N-dimethylacetamide, N-methyl-2-pyrrolidone, N,N'-dimethylimidazolidone, dimethylsulfoxide and sulfolane per 100 parts of said aromatic halide to form a reaction product;
(b) extracting said reaction product from the resultant mixture from a solvent selected from the group consisting of benzene, toulene, xylene, chlorobenzene, dichlorobenzene and 1,1,2-tricholorethane;
(c) washing the extracted solution with an alkaline aqueous solution and water; and
(d) removing solvent and aqueous washing solution to obtain said aromatic nitrile.

* * * * *

UNITED STATES PATENT AND TRADEMARK OFFICE
CERTIFICATE OF CORRECTION

PATENT NO. : 4,959,487

DATED : September 25, 1990

INVENTOR(S) : YAMASAKI et al

It is certified that error appears in the above-identified patent and that said Letters Patent is hereby corrected as shown below:

Column 2, lines 29-30, change "2-bormonitrobenzene" to --bromonitrobenzene--.

Column 7, lines 5 and 6 (claim 2), and lines 26-27 (claim 7), change "2-romonitrobenzene" to --2-bromonitrobenzene--.

Signed and Sealed this

Thirtieth Day of June, 1992

Attest:

DOUGLAS B. COMER

Attesting Officer

Acting Commissioner of Patents and Trademarks